United States Patent [19]

Van Newenhizen

[11] Patent Number: 5,585,003
[45] Date of Patent: Dec. 17, 1996

[54] TREATMENT OF DIALYSIS FEEDWATER USING OZONE

[75] Inventor: John Van Newenhizen, Mundelein, Ill.

[73] Assignee: Culligan International Company, Northbrook, Ill.

[21] Appl. No.: 564,883

[22] Filed: Nov. 30, 1995

[51] Int. Cl.$^6$ .................................................. C02F 1/78
[52] U.S. Cl. .................. 210/646; 210/748; 210/760; 422/28
[58] Field of Search ........................ 210/748, 760, 210/646; 422/28

[56] References Cited

U.S. PATENT DOCUMENTS 4,977,094  12/1990  Goldstein et al. .................... 436/157
5,053,143  10/1991  Miller et al. ......................... 210/321.6
5,336,165  8/1994  Twardowski ......................... 210/646

FOREIGN PATENT DOCUMENTS 2506286  11/1982  France ................................. 210/646

Primary Examiner—Neil McCarthy
Attorney, Agent, or Firm—Gerstman, Ellis & McMillin, Ltd.

[57] ABSTRACT

A process is disclosed for treatment of dialysis feedwater using ozone. The ozone is added to the feedwater storage tank. It is removed prior to use of the feedwater in dialysis using ultraviolet light. A process for disinfecting a dialysis feedwater loop using ozonated water is also provided.

6 Claims, 1 Drawing Sheet 5,585,003

TREATMENT OF DIALYSIS FEEDWATER USING OZONE

FIELD OF THE INVENTION

The present invention concerns a novel method for the treatment of dialysis feedwater.

BACKGROUND OF THE INVENTION

Devices and methods for the purification of water used for dialysis are known. The control of bacteria in the water used for preparing dialysate solutions is critical. It has been reported that elevated levels of bacteria can cause severe pyrogenic reactions in dialysis patients.

This invention provides a means of continuously controlling bacteria in the water produced for dialysis. Other methods currently use periodic disinfection techniques for bacterial control which allows for the reinfestation of the water system between disinfection procedures. These disinfection procedures may also be frequent and lengthy, thus, requiring substantial downtime of the system.

Many conventional water systems for dialysis use a storage tank with a repressurization pump and recirculating distribution loop type of system. This invention overcomes some of the disadvantages of these systems.

In conventional systems, the make-up water system can be shutdown once the storage tank is full. When the make-up system is restarted, bacteria from the make-up equipment can be delivered to the storage tank. Thereafter, bacterial growth can occur in the storage tank. In an illustrative embodiment, this invention addresses this problem by providing a continuous feed of ozone into the storage tank so any bacteria that might be introduced by the make-up equipment after a shutdown is effectively controlled.

In conventional systems, the repressurization pump keeps water moving through the distribution loop at all times, helping to control the formation of biofilms in the piping system. Conventional storage tank systems can carry all the storage tank bacteria build-up into the entire piping system and any piping system contamination back to the storage tank. In the illustrative embodiment discussed above, this invention disinfects the recirculated water every time it is returned to the storage tank.

To overcome the problems of a conventional storage tank system, some current designs eliminate the storage tank and use the make-up water in a direct feed arrangement in an effort to eliminate the problems caused by contamination of the storage tank. There are disadvantages to this type of system that this invention does not suffer from. In such systems, the make-up water treatment apparatus must be of sufficiently large capacity to meet the moment-to-moment demands of the dialysis apparatus.

To keep water moving through the piping at all times, the make-up system must run continuously. This is quite wasteful during periods when dialysis procedures are not being performed and puts a great demand on the make-up system. With this invention, a storage tank may be used without compromising the safety of the system so that the make-up system can be shut down when there is no demand for water.

Also, a direct feed system must use some of the reverse osmosis pumping power to provide pressure in the distribution loop. This subtracts from the available membrane driving pressure reducing performance of the membrane system. In the illustrative embodiment, this invention uses a separate repressurization pump to deliver water to the distribution loop.

Another advantage of this invention is the ease, speed and effectiveness it provides in disinfecting the distribution piping system. Present methods of dialysis piping system disinfection involve large amounts of disinfection chemicals that must be mixed and recirculated. Often this solution is left in the piping system for a period of time to provide good contact kill time. Then the system is rinsed until no trace of the disinfection chemical is detected. Many systems must rinse for extended times to achieve total removal of chemicals and many systems find that they must perform weekly disinfections to maintain low levels of contaminants. These methods are not entirely satisfactory because they require flushing of the system with large quantities of water (which might reinfect the system) to remove all traces of the disinfection chemical and they allow for reinfestation of the system between disinfection procedures. Using this invention, a disinfection procedure is quick and simple.

This invention has the advantage of never having to be shut down during use or for disinfection and water can always be kept flowing through the piping system. This helps control the potential for biofilm growth in the system.

An object of the present invention is to provide a water supply system for dialysis which is disinfected using ozone.

Another object of the present invention is to provide a method for disinfection of dialysis feedwater using ozone which is easy to construct and is simple in operation.

A still further object of the present invention is to provide a method for disinfection of dialysis feedwater and its distribution piping loop using ozone that is effective and economical in use.

Other objects and advantages of the present invention will become apparent as the description proceeds.

SUMMARY OF THE INVENTION

This invention utilizes the powerful disinfection capability of ozone to maintain the bacteriological purity of water used for kidney dialysis. The ozone is removed using ultraviolet light just before the water is delivered to the dialysis water distribution loop. Further, the water with ozone in it can be recirculated through the distribution piping system for disinfection purposes.

In a preferred embodiment, this invention uses conventional pretreatment equipment with a reverse osmosis system to provide make-up water. A stand-by set of deionization ("DI") tanks may be kept ready in the event of a failure in the reverse osmosis system. This invention has the disinfection power to kill the bacteria that could grow in the DI tanks left on stand-by should they be required for immediate emergency use.

From the pretreatment equipment, the make-up water is delivered to a stainless steel storage tank designed for use with an ozone diffuser. Ozone is delivered to the tank from an appropriately sized ozone generator. Water is constantly drawn from the storage tank and delivered to the distribution loop with a properly sized stainless steel pump.

After the pump, two ultraviolet lights are operated in series at a wavelength that will destroy the dissolved ozone in the water. The UV lights are equipped with a performance monitor and one or more alarms. A dissolved ozone monitoring device (or an oxidation potential monitor) follows the UV lights to insure no ozone is delivered in the distribution loop to the dialysis patients. A final filter is used to remove any particles from the water. The distribution loop then runs to the points of use and back to the storage tank through a pressure control valve that maintains the loop at a set pressure.

In order to disinfect the dialysis feedwater distribution loop, the ultraviolet lights used to destroy the ozone in the operating mode are turned off and water from the storage tank containing dissolved ozone is permitted to flow through the entire distribution loop and back to the storage tank. Recycling this water with the UV lights off will allow the dissolved ozone level to increase. The rate of kill with ozone is as much as 3,000 times faster than with conventional chemicals like chlorine, so extended soak times are not required. After a period of recycling, the UV ozone destruct lights are turned back on to remove the ozone from the water being pumped through the loop. The residual ozone is then removed from the loop. Moreover, residual ozone is an unstable compound that decomposes back to the oxygen from which it was made. The rate of decay is dependent upon pH and temperature, but the ozone has typically gone from 0.5 mg/l to 0.0 mg/l in less than 8 hours even without the UV ozone destruct lights. The ease and speed of performing a disinfection rinse cycle may allow systems to be disinfected daily if needed.

A more detailed explanation of the invention is provided in the following description and claims, and is illustrated in the accompanying drawings.

DETAILED DESCRIPTION OF THE ILLUSTRATIVE EMBODIMENT

Figure 1:
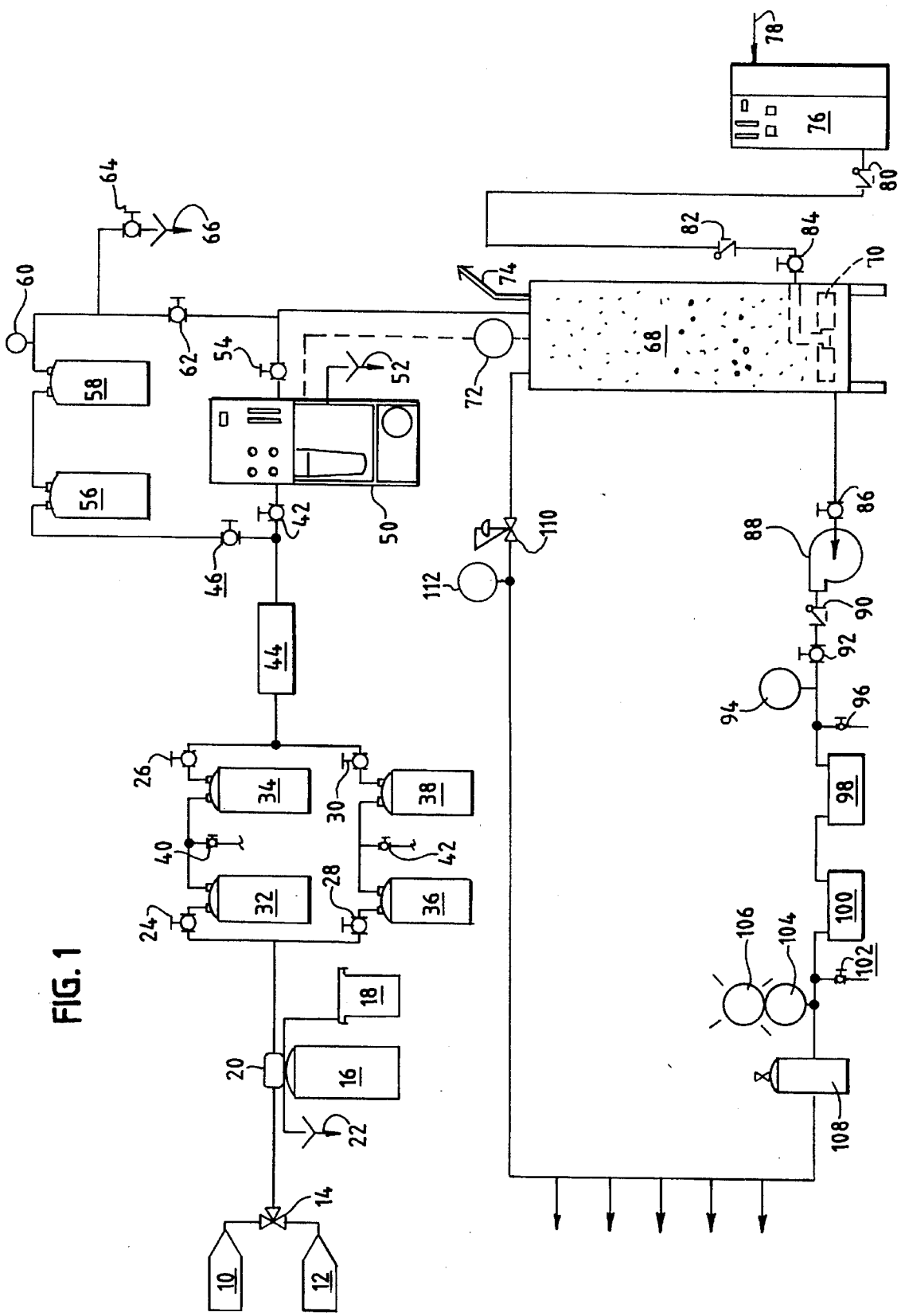
FIG. 1 is a block diagram of an illustrative embodiment of the present invention.

In accordance with the present invention, a water treatment system is shown in FIG. 1. The preferred embodiment of FIG. 1 includes a pretreatment system to supply make-up water (reference numbers 10 through 66), a storage tank (68–74 and ozone supply system 76–84) and a dialysis feedwater loop (reference numbers 86–112).

As shown in FIG. 1, a hot water feed 10 and a cold water feed 12 are provided from the conventional potable water system. Although cold water alone may be used, it is preferred that approximately room temperature water be used. Water which is too cold reacts more slowly to treatment and has a greater capacity for dissolved gases. Using water which is too hot wastes energy and may damage the ion exchange resins, reverse osmosis membranes or other equipment or materials used in treating the water. In order to obtain water within the proper temperature range, a temperature blending valve 14 is used.

In the preferred embodiment of FIG. 1, the water is initially treated using a water softener of conventional design comprising a treatment tank 16, a brine tank 18, a control unit 20 and a drain 22. If the water has been previously softened or the water supply is sufficiently pure, this softening step will not be necessary.

The water is then subjected to activated carbon filtration. In the illustrative embodiment of FIG. 1 there are four activated carbon valves 24, 26, 28, 30, a set of four activated carbon tanks 32, 34, 36, 38 and two drain valves 40, 42. The valves, tanks and drain valves are arranged in two parallel series which each include two tanks, two valves and a drain valve.

After the activated carbon filters, the water is exposed to ultraviolet light 44. The ultraviolet light 44 is used to destroy or reduce biological contamination.

Thereafter, the water travels through either valve 46 or valve 48. The system is designed so that the water preferably is treated in the reverse osmosis (RO) branch consisting of the RO system 50, drain 52 and valve 54. A pair of stand-by deionization (DI) tanks 56, 58 are provided which can be used when the RO system is inoperative.

The DI tanks 56, 58 are connected in series and can contain ion exchange resins. The ion exchange resins will preferably consist of both anion and cation resins. They may be equipped so that one of the tanks contains anion resin and the other contains cation resin or one or more may contain a mixed bed consisting of a mixture of anion and cation resins. A resistivity indicator 60 is provided in order to indicate the quality of the water exiting the stand-by DI tanks 56, 58. Downstream of the resistivity indicator 60 are a rinse-up valve 64 connected to drain 66 and a valve 62.

The water is then fed to a storage tank 68 equipped with an ozone diffuser. The storage tank 68 is preferably made of stainless steel.

The storage tank 68 and the RO system 50 are connected by an electronic level control apparatus 72. The level control apparatus 72 automatically operates to turn the RO system 50 on and off to keep the water at an appropriate level in the storage tank 68.

The storage tank 68 is also provided with a vent 74 to the outside in order to prevent a build up of gas pressure in the storage tank 68 and to vent the ozone into the atmosphere.

Gaseous ozone is supplied to the ozone diffuser 70 in the storage tank 68 from ozone generator 76. The ozone generator 76 takes in air through inlet 78 and produces gaseous ozone. In order to prevent any water from going from the storage tank 68 to the ozone generator 76 through the line used to feed the ozone to the ozone diffuser 70, the line includes two back flow preventing valves 80, 82 positioned on either side of a portion of the ozone feed line which runs a minimum of 2 feet in height above the top of the storage tank 68. An additional valve 84 is also placed in the ozone feed line.

From the storage tank 68, ozonated water is fed through valve 86 to repressurization pump 88. A backflow prevention valve 90 is placed immediately downstream of the repressurization pump to prevent water from flowing backwards in the dialysis feedwater loop. The loop also includes a valve 92, pressure indicator 94 and drain valve 96.

The water is then fed to one or more ultraviolet lights for ozone removal. In FIG. 1, two ultraviolet lights 98, 100 are shown arranged in series. The ultraviolet lights are provided in order to remove the ozone prior to the water being used for kidney dialysis. Thus, they provide ultraviolet lights of a wavelength appropriate for destroying ozone. The UV lights are equipped with performance monitors and alarms to ensure proper and safe operation.

A drain valve 102, an ozone monitor 104 and an alarm 106 are provided. This ozone monitor 104 and alarm 106 function to provide additional assurance that no ozone is present in the water used for dialysis. As a final step prior to use, the water is run through a 0.05 micron filter 108. The water is now very pure and free of a biological contamination and can be used for kidney dialysis.

Any water not used remains in the dialysis feedwater loop and is returned to the storage tank 68 after passing pressure indicator 112 and pressure regulating valve 110. Thus, the returned feedwater is again ozonated.

It can be readily appreciated that the dialysis feedwater loop can be kept free of bacterial contamination by turning off the ultraviolet lights 98, 100 when the dialysis equipment is not being used and circulating ozonated water through the dialysis feedwater loop.

The above has been offered for illustrative purposes only and is not intended to limit the scope of the invention which is defined in the claims below.

What is claimed is:

1. A process for the treatment of dialysis feedwater comprising:

adding ozone to dialysis feedwater in a storage tank;

exposing the ozonated feedwater to ultraviolet light to remove said ozone;

measuring the ozone level in said feedwater; and using said feedwater in kidney dialysis.

2. The process of claim 1 further comprising returning used feedwater to said storage tank and adding ozone to said used feedwater.

3. The process of claim 2 wherein said feedwater is kept in substantially continuous circulation.

4. A process for the disinfection of a dialysis feedwater distribution loop comprising:

adding ozone to dialysis feedwater in a storage tank; and circulating said ozonated water in a dialysis feedwater distribution loop.

5. The process of claim 4 further comprising exposing the ozonated feedwater to ultraviolet light to remove said ozone.

6. A process for the preparation of dialysis feedwater comprising:

removing contaminants from water by treating said water with one or more water treatment methods selected from the group consisting of softening, treatment with activated carbon filters, exposure to ultraviolet light, deionization and reverse osmosis;

substantially sterilizing said water by adding ozone; and removing said ozone prior to using said water for dialysis.

* * * * *